(12) United States Patent
Rozier et al.

(10) Patent No.: US 6,526,981 B1
(45) Date of Patent: Mar. 4, 2003

(54) SITE GUARD FOR INTRAVENOUS SITES AND OTHER SENSITIVE AREAS

(75) Inventors: Betty M. Rozier, Hazelwood, MO (US); Lisa M. Vallino, Ballwin, MO (US)

(73) Assignee: I.V. House, Inc., Hazelwood, MO (US)

( * ) Notice: Subject to any disclaimer, the term of this patent is extended or adjusted under 35 U.S.C. 154(b) by 72 days.

(21) Appl. No.: 09/608,648

(22) Filed: Jun. 30, 2000

(51) Int. Cl.[7] ................................................ A61F 13/00
(52) U.S. Cl. ...................... 128/846; 128/877; 128/878; 128/879
(58) Field of Search ................... 128/877, 878, 128/879; 602/41, 42, 53, 75, 76, 79; 604/179, 180

(56) References Cited

U.S. PATENT DOCUMENTS

| | | | |
|---|---|---|---|
| 3,782,378 A | 1/1974 | Page | 128/133 |
| 4,930,500 A | * 6/1990 | Morgan | 602/48 |
| 5,018,534 A | * 5/1991 | Grant | 128/877 |
| 5,074,847 A | 12/1991 | Greenwell et al. | |
| 5,112,313 A | 5/1992 | Sallee | |
| 5,167,240 A | * 12/1992 | Rozier et al. | |
| D335,926 S | 5/1993 | Rozier et al. | |
| 5,238,010 A | * 8/1993 | Grabenkort | 128/888 |
| 5,336,195 A | 8/1994 | Daneshvar | 604/179 |
| D359,120 S | 6/1995 | Sallee et al. | |
| 5,449,349 A | 9/1995 | Salle et al. | |
| 5,456,660 A | 10/1995 | Reich et al. | |
| 5,577,516 A | 11/1996 | Schaeffer | 128/877 |
| 5,897,519 A | 4/1999 | Shesol et al. | |

FOREIGN PATENT DOCUMENTS

EP    WO8706474    11/1987

OTHER PUBLICATIONS

"Nasal Dressing Holder Saves Nurses Time and Adds to Patient Comfort." RN, Jul. 1994, pg. 77.
"Holder keeps Abdominal Feeding Tubes Comfortably in Place." RN, Mar. 1997, pg. 65.
"Holder Secures Catheter without Adhesive Tape." RN, Jun. 1995, pg. 59.

* cited by examiner

Primary Examiner—Michael A. Brown
(74) Attorney, Agent, or Firm—Mayer, Brown, Rowe & Maw; Joseph A. Mahoney; Christine M. Rebman (57) ABSTRACT

A multipurpose site guard for use at all peripheral and central venipuncture infusion sites, sensitive areas, and for pediatric and adult patients. The guard is a hollow plastic member with a base and a sidewall curved upwardly and inwardly to form a cover which is form fitted to the infusion site under finger pressure and which can be taped in place. Improvements to this invention include holding the guard in place with a fabric connector and cushioning the guard's base with a soft material.

31 Claims, 9 Drawing Sheets fig. 1a fig. 1b fig. 1c fig. 1d fig. 1e fig. 2a.

SITE GUARD FOR INTRAVENOUS SITES AND OTHER SENSITIVE AREAS

FIELD OF INVENTION

The present invention relates to a guard for protecting sites on the body, including a fabric connector that holds the guard in place without applying adhesive to a patient's body.

BACKGROUND OF INVENTION

Parenteral administration of therapy is a common and often life-saving medical technique. Perhaps its most common form is intravenous (IV) infusion, a high volume, high risk, high cost therapy that affects virtually all patient populations in all healthcare settings. In this procedure, a needle breaks a patient's skin and enters a vein, and additional equipment delivers therapeutic infusates such as antibiotics, hydration fluids, hyperalimentation, pain management drugs, chemotherapy drugs, indigestible drugs, or blood products into the body. Similar equipment may drain harmful fluids away from the body, such as fluids accumulating around infected wounds or emptying into colostomy bags. Patients may receive IV or other parenteral therapy for a few hours, a few months, or even years.

On the human body, there are a number of possible venipuncture sites. The scalp, upper extremity and lower extremity contain many peripheral venipuncture sites, while central venipuncture sites may access the vena cava.

The major superficial veins of the scalp are the frontal, superficial temporal, posterior auricular, supraorbital, occipital and posterior facial. In the upper extremity, venipuncture sites include the cephalic, median basilic and median antecubital veins, as well as the dorsal venous arch. The saphenous veins, the median marginal veins and the veins of the dorsal arch of the lower extremities are also used.

Central venipuncture sites include the external jugular, the internal jugular or the subdlavian vein. The inferior vena cava is entered through the femoral vein. Central access to the superior vena cava is commonly achieved through peripherally inserted central catheters known as PICC lines, which may take the place of multiple repeated peripheral IVs.

The selection of an IV site depends on a host of considerations including the age of the patient, condition of the patient, what kind of fluid is to be infused, rate at The simplest way to stabilize the joint between the hub and the supply line and to prevent the needle and catheter from being displaced is with adhesive tape (after application of a transparent dressing that maintains sterility). The supply line tubing is taped to the patient over the transparent dressing and "looped," or directed, back to its source. This loop needs to be secure to prevent mechanical catheter manipulation, so that the needle or catheter is less likely to become dislodged if the tubing is accidentally bumped or pulled. If the venipuncture site is adjacent a joint, the joint is often immobilized.

If the IV equipment is taped but otherwise unguarded, the catheter may still be accidentally dislodged or, in the case of adult patients with impaired senses or involuntary movement and pediatric patients, pulled out by the patient or one of his a caregivers or visitors. A taped but otherwise uncovered infusion site may frighten pediatric patients and be a stressor even to adults, particularly if they are very old or sick.

In addition to tape, devices have been proposed for guarding the needle or catheter at the infusion site and for protecting the joint between the needle or catheter and the supply line. Many of these devices are specially designed for use at a particular infusion site and are big, expensive and mechanically complicated. For example, there are devices with domes over the infusion site and with means for immobilizing the elbow joint for intravenous infusion adjacent the joint of an adult. There are other special purpose devices for protecting the infusion site on a child's scalp and so forth.

The applicants' U.S. Pat. Nos. 5,167,240 and Des. 335,926 teach a hollow member to cover puncture sites made by IV needles (the "I.V. HOUSE"®). Through principles of blow dispersion and absorption, the I.V. HOUSE helps protect sites such as injection sites which are a catheter length away from the infusion sites, as well as venipunctures and their accompanying IV needles and catheters from being bumped or pulled. The I.V. HOUSE is used in the health care industry on adult and pediatric patients.

Hollow members are usually secured in place by adhesives such as tape. However, the use of adhesives is problematic for many patients. Patients may have which the fluid is to be infused and so forth. In general, if the patient is an adult, the best venipuncture sites, in order of preference, are the lower arm and hand, the upper arm, and the antecubital fossa. If the patient is an infant, a scalp vein may be used because it is accessible and when other peripheral attempts have failed.

Needles and catheters of various sorts are used for IV infusions. In the past, the same needle used to puncture the vein was also used for infusing the fluid. Present practice, however, is to infuse the fluid through a catheter that is planted with a needle which is then withdrawn. Currently there are two major types of catheters—namely, over-the-needle catheters and through-the-needle catheters. A third type, steel butterfly needles, formerly used in treating children, have been superseded by over-the-needle catheters.

Old fashioned needles and modern catheters terminate in a hub for connection to a fluid supply line by means of a separable tapered part. The friction joint between the hub and the supply line sometimes becomes detached even with a threaded locking connector such as a luer lock. When this happens, fluid is lost and the patient may be seriously affected beyond the value of the fluid lost. Needles and catheters are also subject to inadvertent displacement whereby the needle or catheter is withdrawn from the vein or perforates the vein's opposite wall causing the infused fluid to infiltrate and swell the surrounding tissue. This thwarts infusion therapy and causes other problems. Displacement of the needle or catheter is particularly likely when the venipuncture infusion site is adjacent a joint.

Agencies such as the Center for Disease Control require that catheters be changed every 48 hours if an institution has an incidence of phlebitis greater than 5%, and every 72 hours if the incidence of phlebitis is less than 5%. However, such agencies seek to extend catheter dwell time to 96 hours. Prolonging the lifespan of peripheral catheters benefits patients by decreasing the number of IV starts, decreasing infection due to fewer needlesticks, decreasing the incidence of thrombus, decreasing the cost of IV start supplies, decreasing nursing time and physiologic cost to the patient, and in some cases, fewer interruptions in nutritional therapy. Also, increasing the dwell time can salvage more veins for use at a later date. external or subsurface conditions adjacent a site that may be irritated or exacerbated by the adhesive's chemicals, by the tape's nonporous nature, or by the mechanical pulling needed to remove the tape. Some patients are immunocompromised or sensitive or allergic to the adhesive, or become so during the course of treatment. The skin of geriatric and pediatric patients, especially neonates, tends to be sensitive even when healthy. Other patients have unhealthy skin, such as patients suffering from diseases of or affecting the skin including but not limited to Stevens-Johnson syndrome, skin cancer, acne, allergic rashes or general dermatitis, and may also be harmed by the use of adhesives. The sensitivity of patients' skin with burns, for example from fire, the sun, contact with chemicals or chemotherapy treatments, presents enormous difficulties in protecting IV puncture sites and other surface or subsurface problems. Many patients have varying concentrations of hair on their skin, making tape painful to remove unless the site is shaved. Patients with these or other skin conditions may suffer mild to severe itching, rashes, blisters, open sores, sloughing of the skin, even scars, among other things, from the use of adhesives on their skin.

Using tape to secure hollow members has other difficulties. When the environment or the patient's skin becomes moist, for instance in humid climates or patients who perspire profusely, adhesives may loosen and thus lose their supportive value. Tape does not adhere well to raw, burned, or otherwise unhealthy skin, or to sites in irregular places such as the head. Adhesives also loosen if they are moved too much, or if they do not have a solid flush surface to stick to. Furthermore, tape can stick to a health care provider's glove and tear it, potentially exposing the worker to bloodborne pathogens and compounding concerns about introducing new infections to a patient.

In view of the above, there is a continuing need for a general-purpose guard for a variety of sites on pediatric and adult patients. However, the use of tape to secure a hollow member over one or more sites creates problems in a variety of patients. The present invention seeks to allay that problem.

SUMMARY OF INVENTION

The site guard of the present invention avoids difficulties with adhesives by securing a protective hollow member to one or more desired sites with a fabric connector that does not use adhesives on patients' skin. Besides protecting patients from exposure to adhesives, the inventive site guard's universal design and use is more adaptable to irregular or hirsute body surfaces than those secured to patients' skin with adhesives. The site guard adapts well to humid environments and allows for better stabilization of IV sites in cases where tape is inadequate or painful, such as on the sensitive skin of geriatric patients and on neonatal and other pediatric patients, and when patients' skin is otherwise moist, sensitive or unhealthy. Overall, the use of a fabric connector to secure a hollow member over a site helps maintain the integrity of healthy and unhealthy skin and keeps it free of irritation.

The site guard of the present invention comprises a hollow member affixed to a fabric connector. The hollow member has a base with an edge to be positioned upon a patient adjacent a site, dimensioned so as to completely cover the site. The fabric connector is removably or permanently affixed to the hollow member to hold the site guard in place over the site. The present invention also includes a method for protecting a site, comprising placing a hollow member over the site and securing it to a patient with a fabric connector that avoids applying adhesive to the patient's skin.

The site guard's easy-to-fasten fabric connector benefits at-home patients; in some embodiments, the entire apparatus may be removed, washed and reused. It also improves stability over tape in active patients apt to dislodge their IV inserts, such as active children, epileptic, delirious or physically aggressive patients, or patients who are simply out of bed and ambulatory.

BRIEF DESCRIPTION OF THE FIGURES

The accompanying drawings illustrate various embodiments of the contemplated invention. Corresponding reference characters refer to corresponding parts throughout the several views of the drawings, and in which.

DETAILED DESCRIPTION OF THE INVENTION

In general, the present invention relates to a site guard comprising a hollow member and a fabric connector to hold it in place over a site without applying adhesive to a patient's skin. The present invention may be embodied in many different forms. The discussion and drawings herein show a few specific embodiments with the understanding that the present disclosure is only an exemplification of the principles of the invention, and is not intended to limit the invention to the embodiments illustrated.

As used herein, "site" includes but is not limited to any wound, any opening, or any lesion in the skin, or more than one wound, opening or lesion, such as those made by needles and those made for catheters, central venipuncture lines, colostomy or ostomy bags, surgical drains; subcutaneous injections, pumps, subcutaneously implanted central venous access devices such as Infusaports®, subcutaneous implanted cardiac devices such as pacemakers and defibrillators; for fistulas used in dialysis. "Site" includes accompanying equipment, for instance equipment present at an intravenous site: a loop of tubing, transparent dressing, and tape, or wound, opening and lesion dressing materials such as gauze. Sites that may benefit from the present invention also include but are not limited by any cut or condition of the skin; and any cut or condition below the skin's surface that could benefit from surface protection, such as bone fractures, tissue swellings, burns, insect bites, excisions, sutures.

As used herein, "hollow member" includes but is not limited to the portion of a site guard dimensioned so as to form a protective cover over a site, including a base with an edge to be positioned upon a patient's skin adjacent a site. Hollow members may be made in a variety of shapes and sizes, such as elongate, circular, square, irregular or any other shaped bases and covers, and small sizes to fit neonates or small body parts. For sites that do not require an open-ended hollow member, for example sites without IV tubing, a fully closed hollow member (FIGS. 7a, 7c) may be used to protect the site, as indicated by a health care provider.

As used herein, "fabric connector" includes but is not limited to one or more pieces of any material, preferably breathable, including but not limited to a tubular material such as a mesh, stretch wrap, burn net, gauze, cotton cloths or blends, latex-free materials, soft cloth, nylon, single or multiple phase polymeric materials such as polypropylene and polytetrahydrofluoroethylene (PTFE, made by Gortex®), tape wrap, a porous mesh, a stretchy fabric, a transparent material such as certain plastic or nylon or blends. Combinations of these materials are also contemplated, as is their treatment with porous polymers such as PTFE. For instance, the use of a porous fabric allows for better protection of patients' surface or subsurface injuries in humid environments, patients with a tendency to perspire, and patients who are active. A stretch wrap may also be useful for active patients, or those whose injuries are located in irregularly contoured areas. A fabric connector could be square, round, tubular, "X" shaped, or any other shape so long as it secures the hollow member to the patient.

One benefit of an "X" shaped fabric connector is to avoid occluding one or more strategically placed ventilation holes. In use, a fabric connector with excess material may be cut to size when a site guard is applied to a patient.

If the entire fabric connector is opaque, a "window" or opening may be made to view a site through a transparent hollow member. Also, one or several windows could be made in the fabric connector to accommodate other sites, or to accommodate body parts such as fingers, eyes, ears or kneecaps. A window could be square, round, "U" or "X" shaped, or any other useful or decorative shape. Models for right or left hands, for instance, may be made. By varying the size or shape of a site guard's hollow member and size, shape, or material of its fabric connector, the site guard may accommodate sites on any desired area of the body, such as infant scalps and extremities.

There are several embodiments of the fabric connector. Some fabric connectors envelop one or more sites, a hollow member and surrounding area; while others comprise one or several straps including means for closing the fabric connector so the entire site guard is secured to a patient. The straps may be simple, such as the elongate fabric connector pictured in FIGS. 1a and 6a, or more complicated such as being made in an "X" or "Y" shape (not shown). "Means for closing" includes but is not limited to a way to fasten a fabric connector 14 such as a strap to the hollow member 12, or two or more straps together to secure the site guard 10 onto the patient. Other fabric connectors are permanently or removably affixed to the inner or outer dome, sidewalls or lower edge of a hollow member. Closure and affixing means or devices include but are not limited to tape and other adhesives such as tape wrap, where fabric is against the skin and a peel-and-stick tape is on both ends, as well as non-adhesives such as hook-and-loop fasteners (Velcro®); Velcro ONE-STRAPs®; ties, pins, clips, ultrasonic welding or glue, and other suitable products. Closure and affixing means are not limited to one shape or size; for instance, Velcro can take any form or shape; circle or square.

A fabric connector may also incorporate or be coated with various agents. As used herein, an "agent" includes but is not limited to antimicrobial agents such as antifungal, antibacterial, or antiviral agents; aloe; vitamin E; lotions; burn salves such as Silvadine, or any other agent. Combinations of these agents may also be used. The amount of each agent used should be sufficient to have the desired effect without irritating the skin or have untoward side effects.

A preferred embodiment of the fabric connector is two straps made of latex-free cloth that fit around an area and attach comfortably to a patient, without being tight or restrictive to medicine or blood flow. It has stretch and memory to retain its original shape, to provide a loose fit that stays in place. The straps attach to each other with some overlap, but do not wrap around the site in a circumferential manner. The ends of the straps are rounded, to avoid leaving unnecessary material for patients to pick at (such superfluous material is often called "dog-eared.") The preferred fabric connector does not require any other fabric connector, such as an ace wrap or a cohesive type wrap that adheres to itself.

Site guards may be stabilized and made more comfortable by cushioning the hollow member's base. Such cushioning may be achieved by affixing various materials to the base, such as cloth, gauze or Gortex-treated materials, or by flaring or otherwise altering the shape of the hollow member's base to make it more stable and comfortable against a patient's skin.

Other potential uses for this product include bracing or supporting bone fractures in areas where the use of casts is difficult or impossible, such as the face. The site guard may be useful in outpatient or over-the-counter settings, for instance for a person with a bumped head to purchase to avoid irritating the bump while sleeping. Also, mammals and other animals may benefit from the present invention.

Figure 1A:
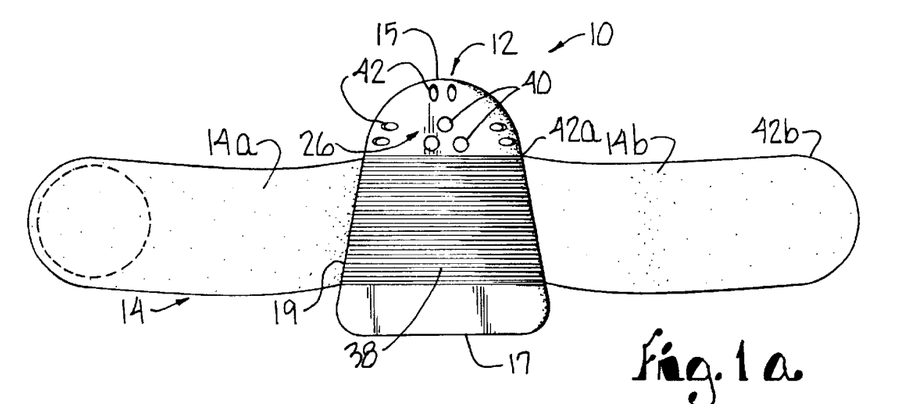
FIG. 1a is a plan view of the top side of the site guard of the present invention, where the fabric connector is affixed to the lower edge and inner sidewall of the hollow member.
Figure 1B:
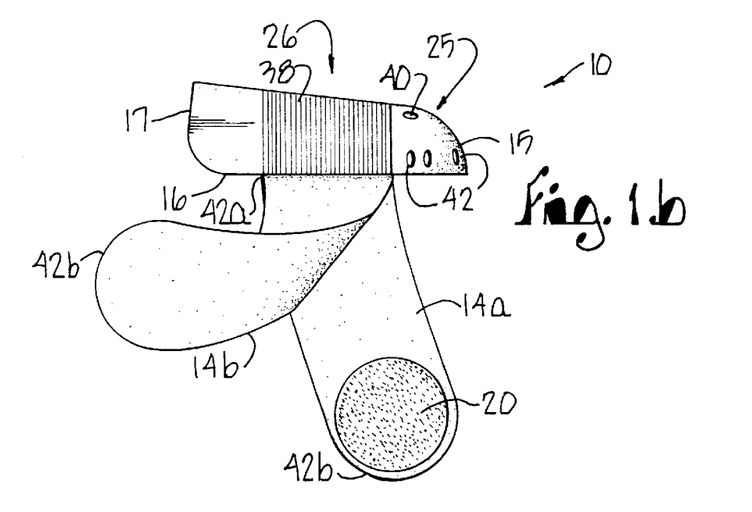
FIG. 1b is a side perspective view of the site guard of the present invention.
Figure 1C:
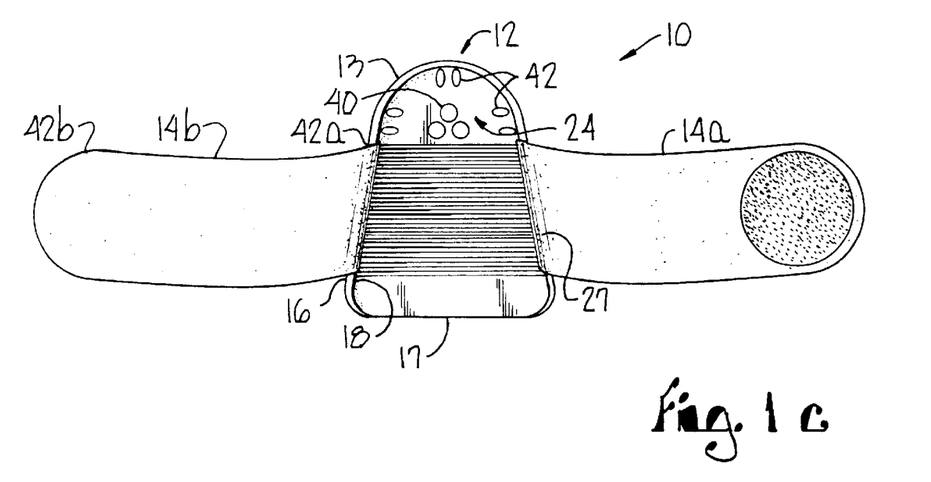
FIG. 1c is a plan view of the bottom side of the site guard of the present invention.

As illustrated in FIGS. 1a–c, reference numeral 10 refers to a site guard, comprised of a hollow member 12 and a fabric connector 14. FIGS. 1a–c illustrate a hollow member 12 that is structurally simple and functionally elegant. It comprises a fabric connector 14 and a hollow member 12 having a U-shaped base 13 with a generally planar lower edge 16. The U-shaped base 13 is joined to sidewalls 18, 19 curved upwardly and inwardly to form a cover 25 with a closed end 15 and an open end 17. The U-shaped base 13 has a width sufficient to straddle a site 48, for instance a site including a needle or catheter 48a, inserted into a vein of a patient where the site 48 also includes a loop of tubing 48c, transparent dressing, and tape 48. The U-shaped base has a length sufficient to cover the site 48 and a height sufficient to provide a space between the inside of the inner dome 24 of the hollow member 12 and the site 48. Another useful embodiment and method for using the site guard 10 includes positioning the hollow member 12 on a patient, where the hollow member 12 has an elongate closed end 15 and the U-shaped base 13 is elongated or split into two legs that may lay flush against the patient's skin (not shown).

Hollow members 12 may be of any size so as to accommodate different sizes of sites 48. For instance, a small I.V. HOUSE has a width of up to about 1.5 inches, a length of up to about 1.5 inches, and a height of up to about 0.5 inch. A large I.V. HOUSE has a width of up to about 2.5 inches, a length of up to about 2.8 inches, and a height of up to about 0.8 inches. Other hollow member 12 dimensions may be useful to protect other sites 48, especially those sites 48 with equipment such as IV equipment 48a–48d, extension sets, Statlocks or Veniguards. Smaller hollow members 12 may be used to accommodate neonates or small animals, and larger hollow members 12 used to accommodate adults or large animals. Both sizes may be used on patients of any age or animals of any size. The hollow member 12 size is determined by the area of the site it encompasses, but is not intended to encompass an entire body or limb. Its dimensions are limited by the size and shape of the base, which contacts patients' skin, and the height of the dome, which protects without becoming unwieldy.

Once the hollow member's dimensions are set, for example to the size of the small or large I.V. HOUSEs described above, in use it will stabilize and standardize the size of the loop of tubing 48c used in sites such as IV sites. Stabilizing the loop of tubing 48c decreases IV therapy problems caused by loops that are too wide or too long. The loop must fit under the hollow member 12 of such sites 48; while varying sizes of tubing 48b and loops 48c may be used, they cannot exceed the dimensions set by the hollow member 12.

Use of the present invention will increase dwell time in patients by decreasing the mechanical manipulation of, for instance, a catheter 48a at a site 48. Anecdotal evidence showed catheters 48a protected by I.V. HOUSEs lasted four to five days in pediatric (less than 18 year old) patients. Accordingly, the site guard 10 can increase dwell time in patients.

The hollow member 12 is formed of a plastic material stiff enough to cushion a site 48 from a blow, and flexible enough such that the U-shaped base 13 can be spread when finger pressure is applied to the cover. To facilitate spreading of the U-shaped base 13 to conform the hollow member 12 to the site 48 and to avoid gouging the patient's skin, it is preferred that the U-shaped base 13 be outwardly flared and that the sidewalls 18,19 be curved at the open end 15 of the hollow member 12 as it joins the base 13.

One suitable material for making the hollow member 12 which satisfies the above-mentioned specifications is medical grade low density polyethylene from which a 0.030 inch thick hollow member 12 is manufactured by injection molding and thermoforming. Other materials and processes, including but not limited to vacuum molding and thermoforming, may be selected to make a rigid or soft or transparent site guard 10. For instance, if a site did not require a flexible hollow member 12, the hollow member 12 could be thermoformed of a polypropylene material to increase its transparency.

Figures 1D, 1E:
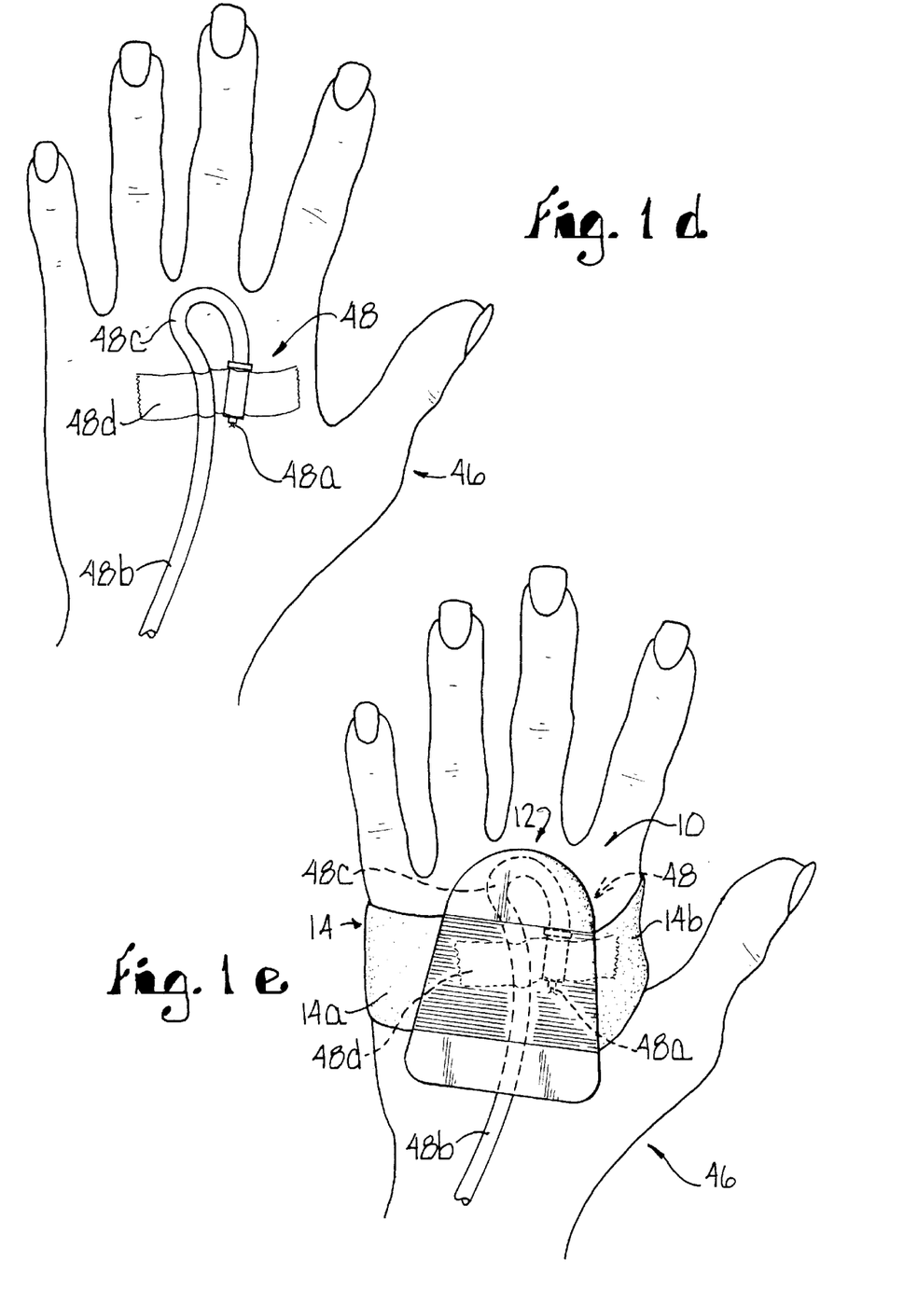
FIG. 1d is a plan view of a hand with a site.
FIG. 1e is a plan view of a hand with a site covered by a site guard.
Figure 5A:
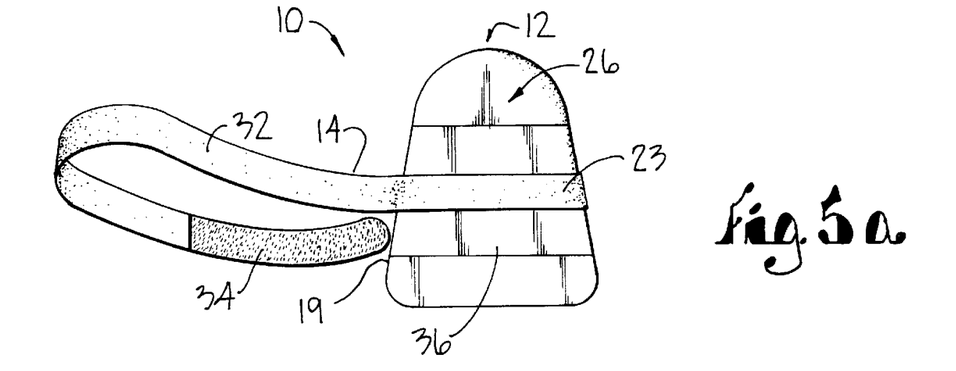
FIG. 5a is a plan view of the top side of the site guard of the present invention, where the fabric connector may be removably affixed to the outer dome and outer sidewall surfaces of the hollow member.
Figure 5B:
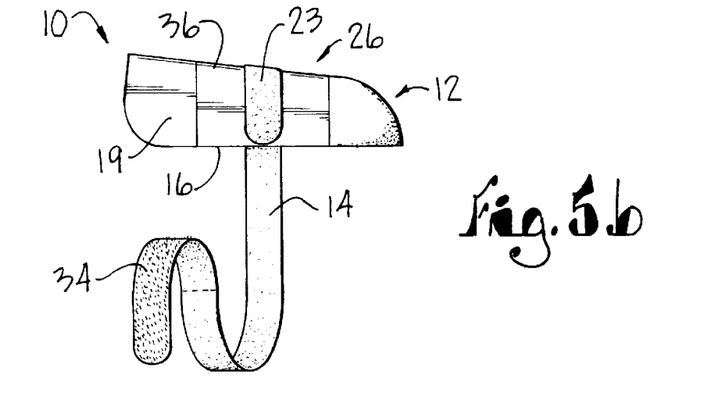
FIG. 5b is a side perspective view of the site guard of the present invention.
Figure 5C:
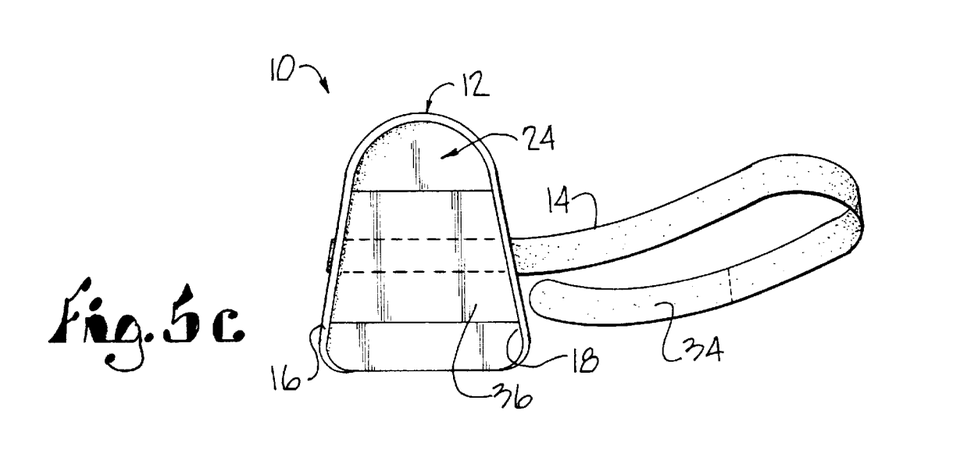
FIG. 5c is a plan view of the bottom side of the site guard of the present invention.
Figure 5D:
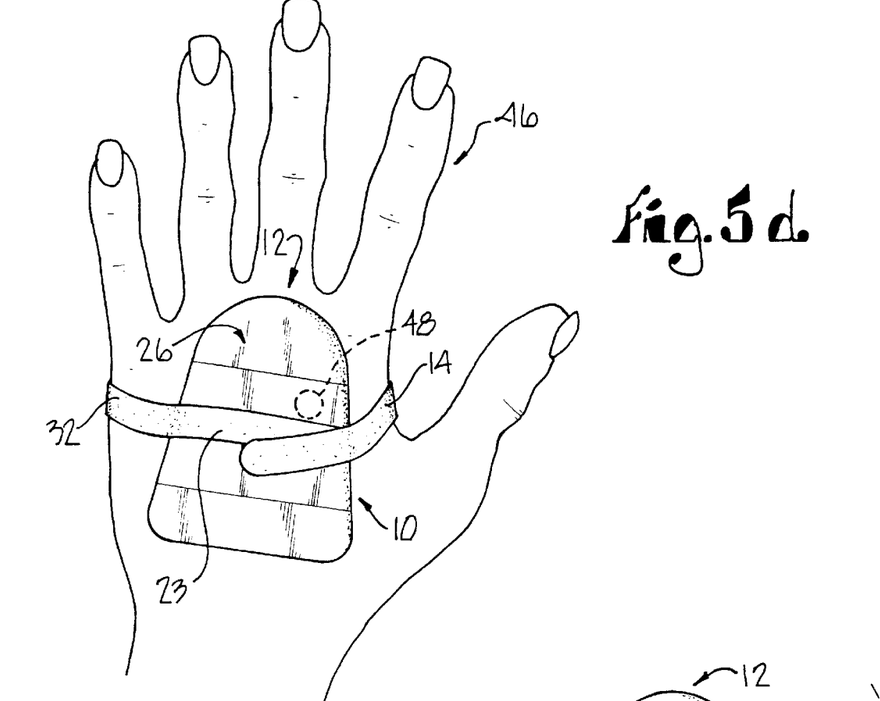
FIG. 5d is a plan view of the site guard covering a site on a hand.
Figure 7A:
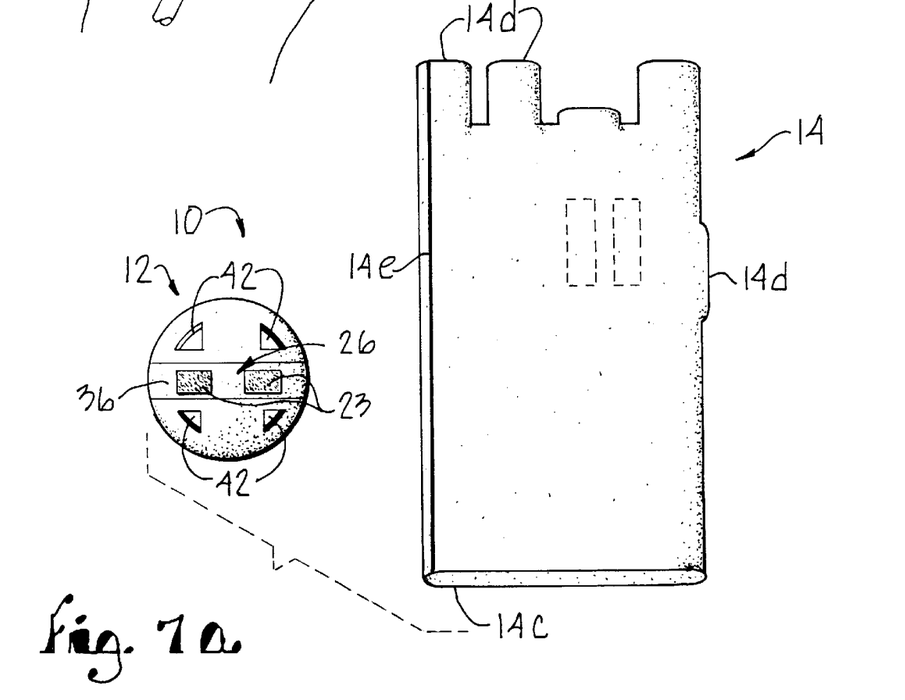
FIG. 7a is a plan view of the site guard of the present invention, where the tubular mesh fabric connector is completely separate from the hollow member.
Figures 7B, 7C:
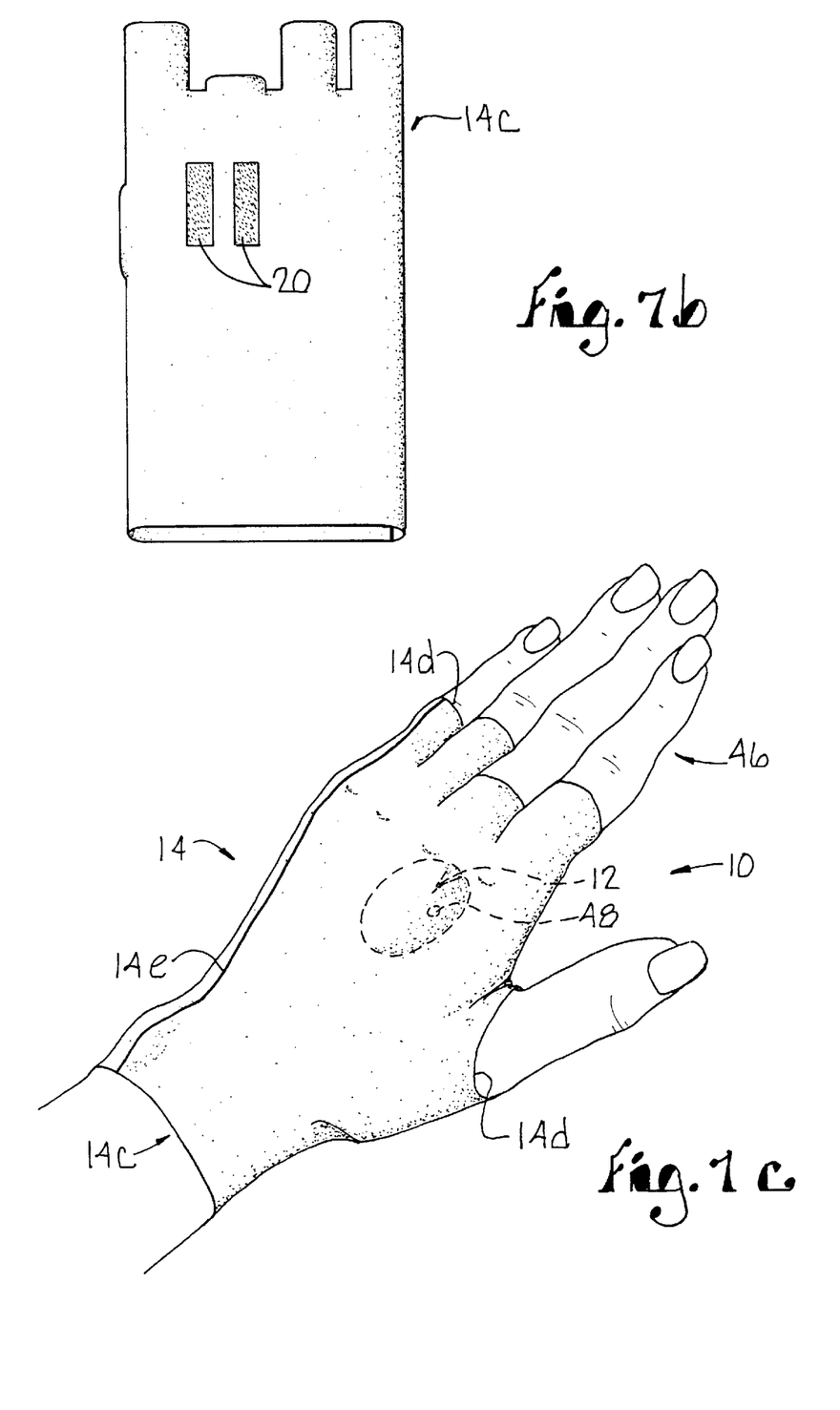
FIG. 7b is a side perspective view of a tubular fabric connector, turned inside-out to expose Velcro strips inside the fabric connector.
FIG. 7c is a side perspective view of the site guard of the present invention, completely assembled, with the fabric connector affixed to the hollow member.

In use as shown in FIGS. 1e, 5d, and 7c, a site guard's 10 hollow member 12 may conform to one or more sites 48 on a hand 46. The hollow member 12 may also conform to venipuncture sites 48 on adults and, on a smaller scale, on infants. The flexibility of the plastic cushions blows on the hollow member 12 with a gradual resistance such that the site 48 is protected, the friction joint between hub and tapered part of hub is not broken, and if present the needle or catheter 48a is protected from displacement. There is a decreased chance of snagging the needle or catheter 48a, which gives the patient a sense of security. The site guard 10 slides easily under covers, loose clothing, and various wraps (FIG. 7), where it can be worn (for instance by IV patients between treatments) without detection and with discretion to protect the patient's right to privacy regarding treatment and illness. Under the protection of the hollow member 12, tubing 48b and other site apparatus, or an extension set that allows infusing through the hub about six inches away from the catheter hub (not shown) rather than directly into the hub on the patient's skin, is separably connected to the hub of a needle or catheter 48a. A setup for a particular patient may or may not employ an extension set. For intermittent use, the hub can be capped with a locking plug (not shown) and the supply line disconnected.

The hollow member's 12 lower edge 16 may have a means, such as a smooth lower edge, a tear drop shaped bead or the like, for spreading the weight of the hollow member 12 across a patient's skin once appropriately placed over a site. Flaring (not shown) or any other modification of any part of the hollow member 12 that directly contacts the skin may act as a "cushion" to further protect the patient's skin or body. The lower edge 16 may be partially cushioned 27 or entirely cushioned 28. For instance, in FIG. 1c the lower edge 16 of the hollow member 12 is partially cushioned 27 by the fabric connector 14, and in FIG. 3c the entire lower edge is cushioned 28 by the fabric connector 14. Material to cushion the lower edge 16 of a hollow member 12 may be made of, but is not limited to, soft porous cloth, gauze, stretch wrap, foam tape, or other suitable substance. Such material is affixed to the hollow member through removable or permanent means like Velcro, sewing, gluing, ultrasonic welding, and any other means for attaching the fabric connector 14 to the hollow member 12. A cushion 27, 28 may improve the stability of a site guard 10 and create a more comfortable fit on the patient's skin. Other uses for a partial 27 or total cushion 28 include monitoring and helping control the moisture inside a hollow member 12, especially for a completely closed hollow member 12 (FIG. 7c), or a hollow member 12 fully enveloped by a fabric connector (FIG. 7c). Site guard 10 cushions 27, 28 may be removably or permanently affixed to the hollow member 12, depending on the type of material the cushion is made from, whether it is part of the fabric connector 14, and the perceived needs of the applicants.

For the purpose of visualizing a site 48 through the hollow member 12 it is preferred that the material comprising the hollow member be transparent or semi-transparent. Transparency is important since the site guard 10 not only acts as an enclosure but also allow visual inspection of the site 48, of the condition of the skin surface immediately around the site, and, if present, of needle or catheter 48a and surrounding areas. The fabric connector 14 may complement this transparency. The fabric connector 14 may be transparent itself; may have a window (opening) 30 cut out of it so the site 48 can be seen (FIGS. 4a, 4c and 6a, 6b), or to accommodate other body parts or other sites; or it may cover the hollow member 12 only a little or not at all (FIGS. 1a–c, 2a–c, 3a–c).

The site may be ventilated. Ventilation is desirable for reasons including but not limited to facilitating an exchange of air to prevent the formation of moisture vapor. Hollow members 12 may be made with one or more ventilation holes, preferably in its top 40 and/or sidewalls 42 (FIGS. 1a–c, 3a–c, 7a and 7c), and preferably its closed end 17. However, a ventilation hole 40, 42 may be placed anywhere on the hollow member 12, and the hollow member 12 may be altered (for instance, by texturing and depressing a means for retaining the fabric connector 14) to enhance ventilation. A ventilation hole 40, 42 may be made in a variety of shapes and sizes, including but not limited to circular, oblong, oblate, elongate, rectangular, square, triangular, or grid-like (for instance, like a screen); as well as being made with a third dimensional variation such as rectangular strips turned inward. Also, a ventilation hole 40, 42 may be covered with a porous material (not shown), such as a plastic grid, nylon mesh, and the like, to provide further protection of the site 48 from invasive particulate or other matter. Alternatively, the site guard 10 may be completely without a ventilation hole.

A preferred embodiment of the site guard 10 is a fully ventilated device where the hollow member's 12 lower edge 16 may be affixed to a fabric connector 14. As indicated above, an affixing means or device includes but is not limited to sewing, gluing, ultrasonic welding, chemical bonding, or using other means such as Velcro to affix the hollow member's 12 lower edge 16 onto a fabric connector 14, such as a cloth or plastic wrap-around dressing. Another embodiment of the site guard 10 affixes the hollow member 12 to the fabric connector 14 by using gauze, flannel or other soft breathable cloth cut on a bias, doubled with a pocket the hollow member 12 can slide into. Another embodiment of the site guard 10 includes ultrasonically welding a fabric connector 14 to a hollow member 12, where the hollow member's 12 lower edge 16 has a flat flange shape. Another embodiment may entail affixing a polyethylene hollow member 12 to a polypropylene fabric connector 14 with a cyanoacrylate system.

A site guard 10 may be provisioned with a "means for retaining" a fabric connector 14 to help secure the site guard 10 to a patient. For example, in FIGS. 1a–c the retaining means is located in the cover 25 between the open end 15 and closed end 17 of the hollow member 12 and is a channel 36 formed in the hollow member 12. The channel may be smooth 36 or grooved 38 or otherwise textured or shaped to help secure a fabric connector 14 in place. As defined herein, retaining means or devices for the fabric connector 14 includes but is not limited to a structure equivalent to a channel 36, such as guiding hooks or half or whole "belt" loops, or could include one or more smaller deeper channels within a larger channel for retaining fabric connectors 14 of varying widths (not shown).

In several embodiments of the invention, the site guard 10 may be easily disengaged from the patient by removing part or all of the fabric connector 14 from the hollow member 12, or by disengaging the site guard 10 from the patient. The integrity of a site 48, and if present a site's 48 needle or catheter 48a, loop of tubing 48c or other accompanying equipment, as well as the patient's skin, may be inspected, treated or adjusted, and the site guard 10 easily remounted. By protecting the site 48, while leaving it readily available for inspection either through the cover 25 or with the cover removed, the number of IV restarts is reduced. The reduction in IV starts reduces patient discomfort and lowers medical costs.

The accompanying drawings illustrate several embodiments of the site guard 10. In every embodiment of the present invention, the site guard 10 may include one or more windows 30 in the fabric connector 14 for viewing the site 48, to avoid harming sites 48 that would otherwise be covered by the fabric connector 14, or to accommodate digits or other body parts otherwise covered by the fabric connector 14 (for example, as shown in FIGS. 3c, 4a, 6a, 7c), or as otherwise desired; one or more channels 36 in the hollow member 12 to help retain the fabric connector as placed with the hollow member 12; ventilation holes 40, 42 in the hollow member 12 to keep the site aerated and otherwise control the environment inside the hollow member 12; antimicrobial or agents; and a cushion 27, 28 on the lower edge 16 of the hollow member 12, in addition to any other accessories indicated or their equivalents. Also, the outer portion 42 of single 14a or opposing straps 14a, 14b, or other portions of a fabric connector 14 may be bifurcated or otherwise splayed; long or short; rounded, flared, tapered, or otherwise shaped. Splayed fabric connectors 14 may be particularly useful for accommodating fingers or other body structures in fastening the site guard 10 to a patient. Site guards 10 may also sport different colors or designs, for example for decorative or classification purposes.

FIG. 1a shows a plan view of the top side of the site guard 10 of the present invention, and FIG. 1b shows a side perspective view. As seen in FIG. 1c, the fabric connector 14 comprises two opposing straps 14a, 14b, each strap having an inner portion 42a affixed to the lower edge 16 and inner sidewall 18 of the hollow member 12. An outer portion 42b includes closure means in the form of a Velcro strip 20. The dimensions of the opposing straps 14a, 14b of this fabric connector 14 are at least about three inches long, and at least about one inch wide. Circular and oval top 40 and side 42 ventilation holes help aerate the site 48. The site guard 10 fabric connector 14 in these illustrations is made of stretch wrap that fastens to the Velcro strip 20, so the relative tightness of the fabric connector 14 may be easily adjusted.

The illustration in FIG. 1c shows that the inner portions 42a of the fabric connector 14 form a partial cushion 27 of the lower edge 16 of the hollow member 12. Covering the lower edge 16 in this way comfortably cushions the patient's skin from direct contact with the lower edge 16. Alternatively, if the fabric connector 14 is not made of a material appropriate for use as a cushion, or if as in other embodiments it is not attached to the lower edge 16 of the hollow member 12, a cushion 27, 28 may still be added to increase patient comfort. FIG. 3c illustrates the complete cushioning 28 of the hollow member's 12 lower edge 16 with the fabric connector 14; as indicated previously, materials other than the fabric connector 14 may also comprise a partial or entire cushion 27, 28.

FIG. 1d shows a hand with an IV site 48, and FIG. 1e shows the site guard 10 assembled over the site 48. In FIG. 1d, the loop 48c extends up among the fingers of an IV patient's hand, then hangs off of the side of the hand. In FIG. 1e, the hollow member 12 controls the size of the loop of tubing 48c, and prevents unnecessary pulling or other movement of the tubing 48b near the puncture area 48. Currently, nurses are instructed to loop 48c the tubing 48b back and secure the tubing with tape 48d. A loop of tubing 48c that is too wide or long creates problems in IV therapy. The hollow member's 12 size and shape stabilize and standardize the size of the loop 48c and tubing 48b used, and thus decrease some IV therapy problems. Adherence to directions facilitates training nurses in the use of this invention without criticizing current practices.

Figure 2A:
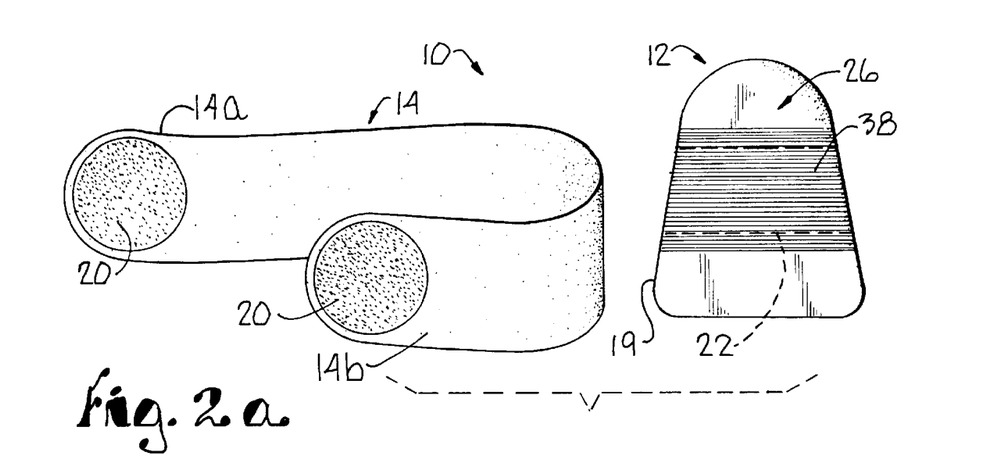
FIG. 2a is a plan view of the top side of the site guard of the present invention, where the fabric connector is completely separate from the hollow member.
Figure 2B:
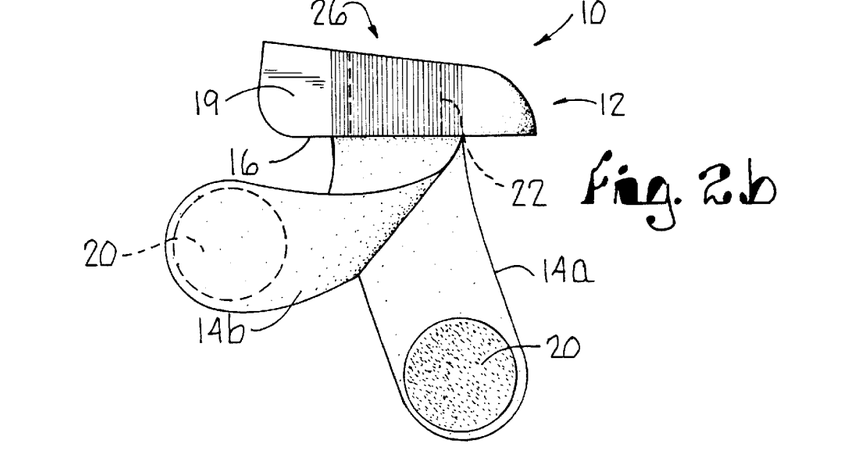
FIG. 2b is a side perspective view of the site guard of the present invention, where the fabric connector is removably affixed to the inner dome of the hollow member.
Figure 2C:
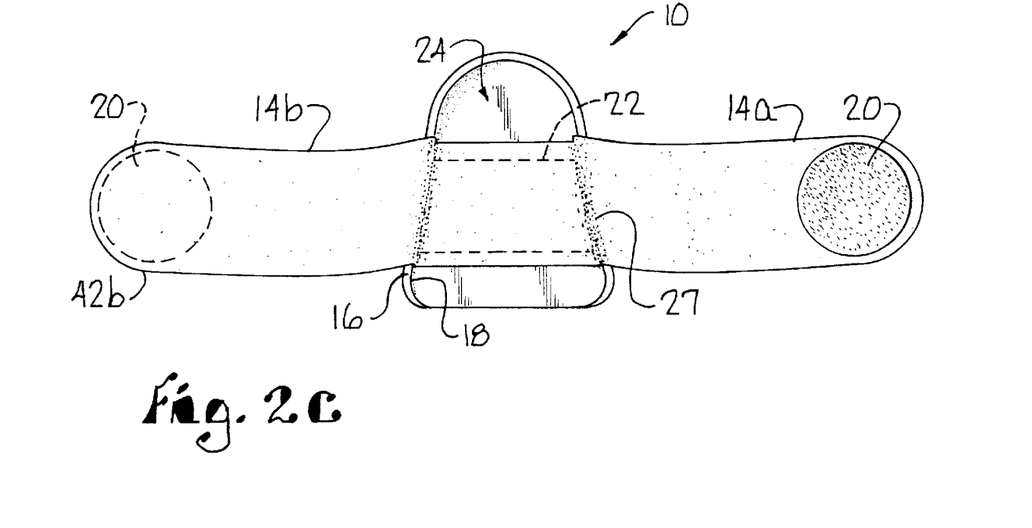
FIG. 2c is a plan view of the bottom side of the site guard of the present invention, where the fabric connector is removably affixed to the inner dome of the hollow member.

The fabric connector 14 in FIG. 2a is completely separate from the hollow member 12; in FIGS. 2b and 2c, the fabric connector 14 is affixed to the interior of the hollow member 12. FIG. 2c shows that the hollow member 12 has affixing means attached to its inner dome surface 22. In this embodiment, the affixing means is a hook and loop fastener like Velcro. The fabric connector 14 is pressed against the Velcro strip 22 in the hollow member 10 to form a site guard 10 that can be placed over a site 48. The fabric connector's opposing straps 14a, 14b may be stretched to comfortably secure the hollow member 12 to a site 48, using closure means such as Velcro strips 20 on the outer portions 42b of the fabric connector 14. A fabric connector 14 affixed in this way to the hollow member 12 automatically creates a partial cushion 27 on the lower edge 16.

Figure 3A:
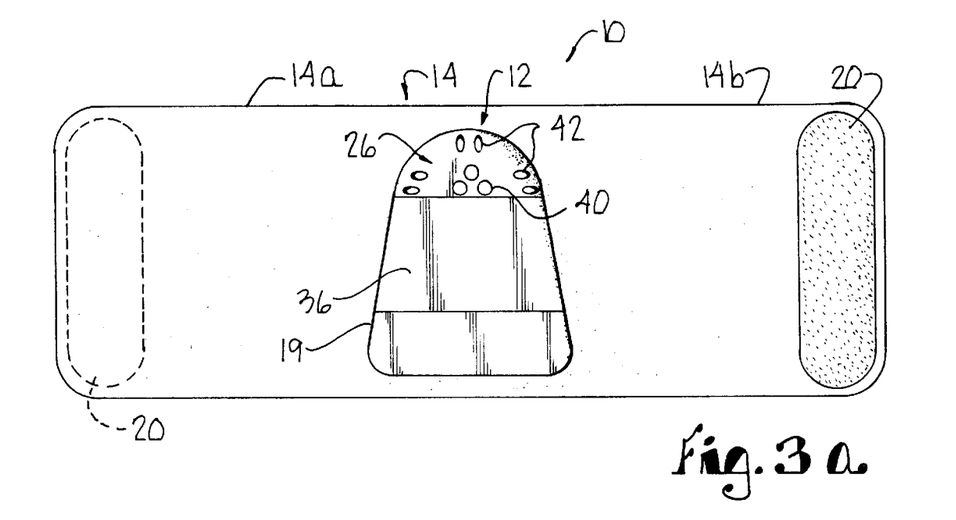
FIG. 3a is plan view of the top side of the site guard of the present invention, with the fabric connector affixed to the lower edge and inner sidewall of the hollow member.
Figure 3B:
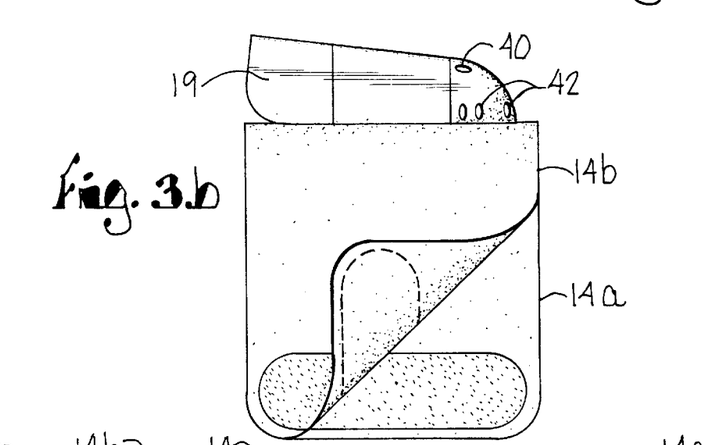
FIG. 3b is a side perspective view of the site guard of the present invention.
Figure 3C:
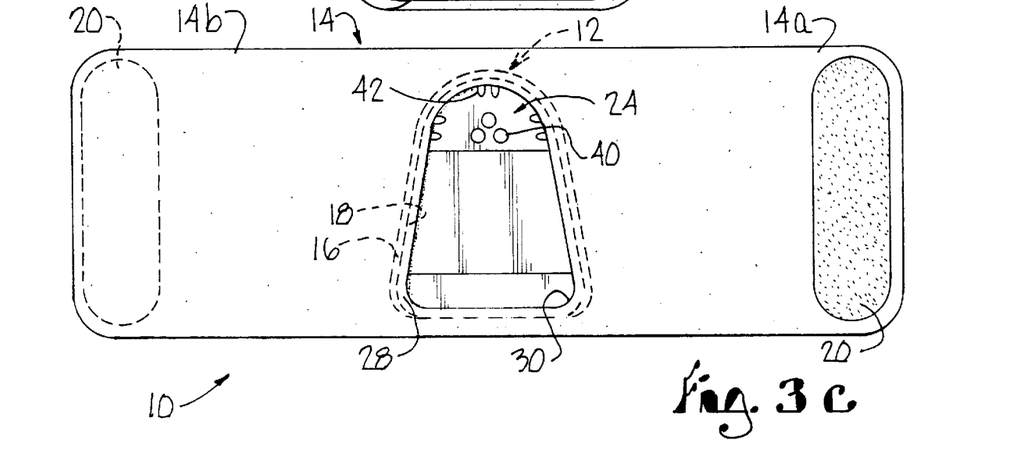
FIG. 3c is a plan view of the bottom side of the site guard of the present invention.

The site guard 10 embodiment illustrated in FIGS. 3a–c is similar to that of FIGS. 1a–c. However, in FIGS. 3a–c the fabric connector 14 is large enough to cover the entire length and width of the hollow member 12, and is affixed to the lower edge 16 of the hollow member 12. The dimensions of the opposing straps 14a, 14b of this fabric connector 14 are at least about two inches and at least about six inches long, and at least about three inches wide. To accommodate the site 48, a window 30 is cut out of the fabric connector 14, as seen in FIG. 3c. The window 30 also preserves the transparency of the hollow member 12, so the site 48 may be fully viewed through the hollow member 12 at all times. The window 30 also creates a complete cushion 28 around the lower edge 16 of the hollow member 12. As in the other examples, the opposing straps of the fabric connector 14a, 14b may be stretched to secure the site guard 10 over the site 48 and closed with Velcro strips 20.

Figure 4A:
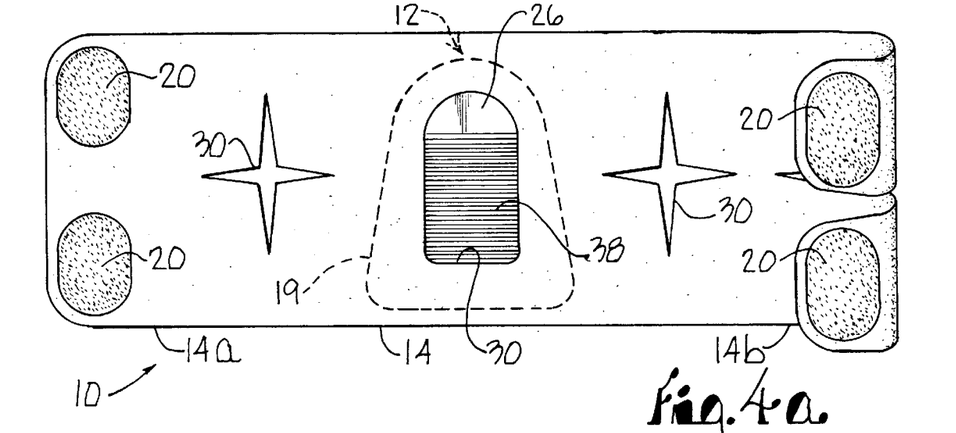
FIG. 4a is plan view of the site guard of the top side of the present invention, with the fabric connector affixed to the outer sidewall of the hollow member.
Figure 4B:
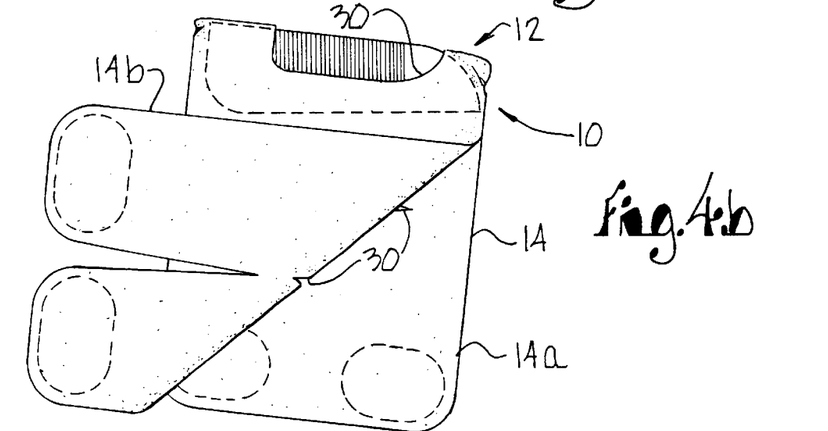
FIG. 4b is a side perspective view of the site guard of the present invention.
Figure 4C:
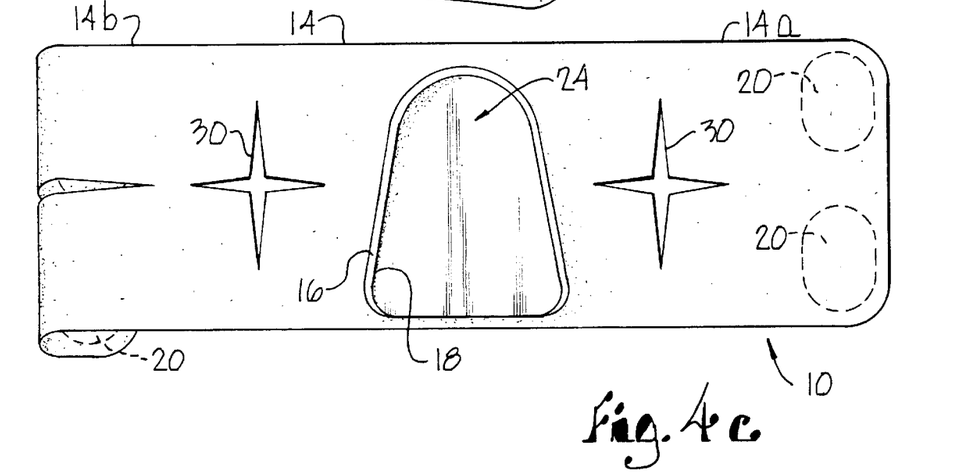
FIG. 4c is a plan view of the bottom side of the site guard of the present invention.

FIGS. 4a–c shows another embodiment of the invention, where the fabric connector 14 is affixed to the outer side walls 19 of the hollow member 12. A window 30 allows for viewing of a site 48, other windows in the opposing straps 14a, 14b of the fabric connectors may accommodate other sites or body parts, and Velcro fasteners 20 close the straps to secure the site guard 10 over a desired site 48. One strap 14b is bifurcated, allowing for greater flexibility in adjusting the fabric connector 14.

FIG. 5a illustrates a plan view of the top side of the site guard of the present invention, where the fabric connector 14 may be removably affixed to the outer dome 26 and outer sidewall 19 surfaces of the hollow member 12. The applicants demonstrate the use of a Velcro ONE-WRAP strap, where Velcro is affixed to the outer dome 26 surface and sidewalls 19 of the hollow member 12. The remainder of the strap is a fabric with a smooth surface 32 and a textured surface 34 that fastens to the Velcro strip, as shown in use in FIG. 5d. The hollow member 12 may thus be secured over a site 48 simply by fastening the textured surface 34 to the Velcro strip.

Figure 6A:
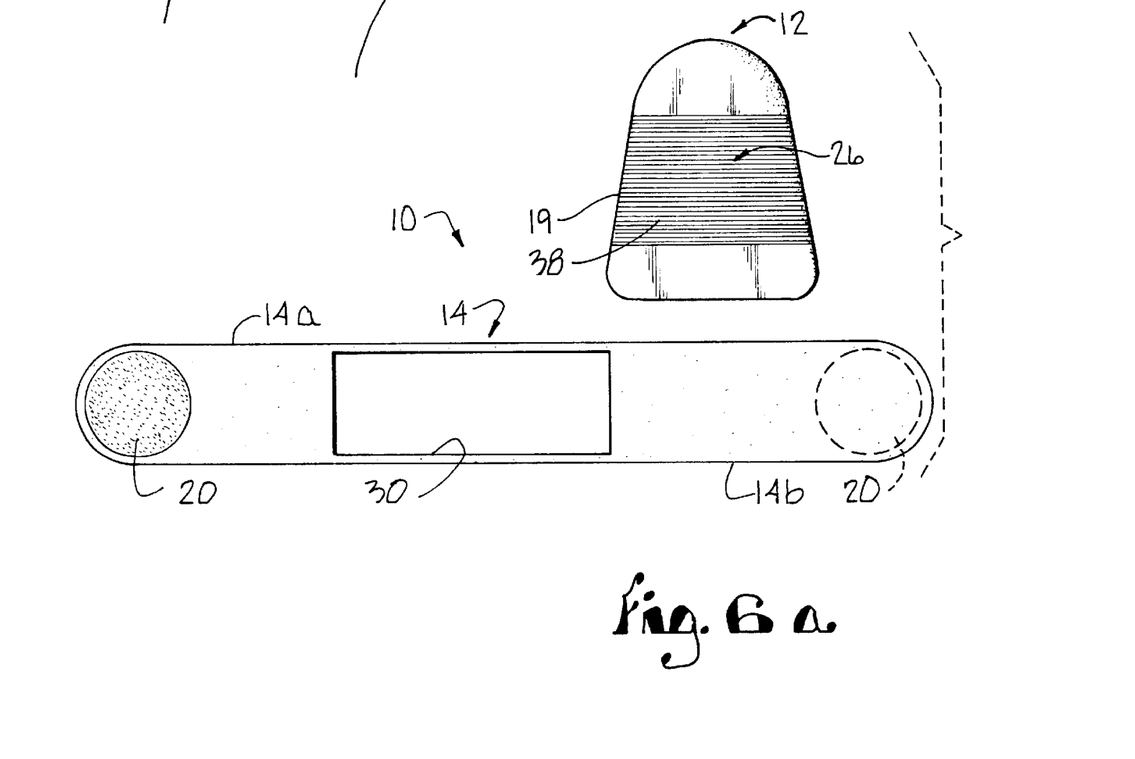
FIG. 6a is a plan view of the top side of the site guard of the present invention, where the fabric connector is completely separate from the hollow member.
Figure 6B:
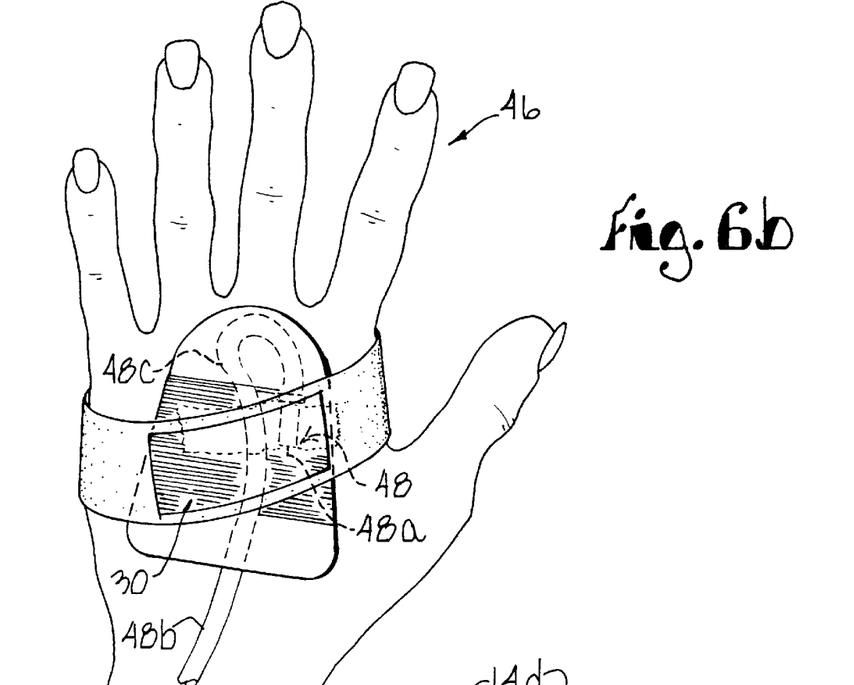
FIG. 6b is a plan view of the site guard of the present invention, completely assembled.

FIG. 6a illustrates an embodiment of the invention where the fabric connector 14 is not permanently affixed to the hollow member 12. FIG. 6b shows the assembly of a site guard 10 over a site 48 on a patient's hand 46. First, a hollow member 12, with or without a cushioned base 27, 28, is placed over a site 48 such that the site and its accompanying tubing 48b and other items fit under the hollow member 12. Then a fabric connector 14 with opposing straps 14a, 14b is placed over the hollow member 12 and secured to the hand with Velcro strips 20 on the outer portions 42b. A channel 38 in the hollow member 12 guides the fabric connector 14 to keep it from becoming displaced. A window 30 in the fabric connector 14 positions over the transparent hollow member 12 so the site 48 can be easily viewed. A Velcro strip 20 placed directly on the outer surface of the hollow member 12 may be used to more fully secure the fabric connector 14 to the hollow member 12.

FIGS. 7a–c illustrate another embodiment of the present invention. FIG. 7a shows a completely closed hollow member 12 with a round base and lower edge 16, and a separate fabric connector 14 made of a delicate white tubular mesh 14c. The fabric connector 14c could be made of any tubular material capable of enveloping a patient's entire hand 46, or any other body part as needed. If a site 48 does not include IV tubing 48b or other apparatus that requires an open end 15 to the hollow member 12, the hollow member 12 may still have one or more open ends 15, or be fully closed 17 as shown here. The lightweight mesh 14c must be tight enough to secure the guard but not so tight as to cause patient discomfort. As seen in FIG. 7b, where the tubular mesh 14c is turned inside-out, the tubular mesh 14c has Velcro strips 20 that will match up with Velcro strips 23 on the outer portion of the hollow member 12 (FIG. 7a), to affix the fabric connector as seen in FIG. 7c.

FIG. 7c shows the fully assembled site guard 10, where the fabric connector 14c completely envelops the hollow member 12 and surrounding area of the patient's hand and wrist. Other means for affixing the fabric connector 14c to the hollow member 12 may also be used. Varying grades of mesh may be used, with the size of the mesh and weight of the material varying with the degree of support needed and the sensitivity of the patient's skin. A window 30 could be made in the fabric connector 14 if the mesh was too dense to allow for viewing of the site. This embodiment provides an exceptionally useful means for securing a hollow member 12 to burn patients, since it is very lightweight, easily removed by cutting, and less dense than fabric connectors 14 comprised of straps. It may also partially conceal the hollow member 12 for cosmetic purposes.

The preferred embodiment of this type of site guard 10 is a fabric connector 14 of tubular shape 14c and of the size to cover a patient's hand and portions of the patient's fingers and wrist. The tubular mesh 14c may have different diameters 14d, 30 to comfortably fit both a narrow wrist and broader hand. The mesh covering the fingers may be cut to various lengths; in the picture, the mesh covering the thumb and middle finger is shorter than the mesh covering the remaining fingers. Fabric connectors 14 may be made to be aesthetically pleasing. In FIG. 7c, a colored stripe 14e runs along the fabric connector 14c from the wrist to the fingers.

Other embodiments of this particular version could include having a ½ length tubule of burn netting permanently or removably attached to the lower edge 16 of the hollow member 12. The fabric connector 14 could be made of stretch wrap or of some more rigid cloth, such as the type that could be comfortably opened, closed and adjusted with crisscross ties like corset strings. Also, a fabric connector 14 could be opened and attached to the base 16 or sidewalls 18, 19 of the hollow member 12, creating an embodiment similar to FIGS. 1a, 3a and 4a, but where the straps are continuous (not shown).

Although the invention has been described with respect to specific embodiments, it should be appreciated that other embodiments utilizing the concept of the present invention are possible without departing from the scope of the invention. The invention, for example, is not intended to be limited to the specific materials discussed and exemplified and disclosed in these embodiments; rather the invention is defined by the claims in equivalence thereof.

What is claimed is:

1. A site guard, comprising:
   a) a hollow member having a base with an edge to be positioned upon a patient adjacent a site, the base having a width sufficient to straddle the site and a length and a height sufficient to cover the site, the base joined to a sidewall to form a cover; and
   b) a fabric connector having a first end and a second end, the first end affixed to the edge of the hollow member and the second end having a closure means, wherein the connector is capable of holding the site guard in place over the site without the need for a separate adhesive tape.

2. The site guard as recited in claim 1 further comprising a second fabric connector having a right end and a left end, the right end affixed to the edge of the hollow member and the left end having a closure means, wherein the closure means of the left end detachably couples to the closure means of the second end.

3. The site guard as recited in claim 2 wherein the fabric connector comprises a material selected from the group consisting of tubular material, tubular mesh, stretch wrap, burn net, gauze, cotton cloths or blend, latex-free material, soft cloth, nylon, polymeric material, polypropylene material, polytetrahydrofluoroethylene (PTFE), transparent plastic material, and combinations of any of the foregoing.

4. The site guard as recited in claim 3 wherein the fabric connector further comprises an agent.

5. The site guard as recited in claim 4 wherein the agent is selected from the group consisting of an antimicrobial, an antifungal, an antiviral, aloe, vitamin E, and combinations of any of the foregoing.

6. The site guard as recited in claim 3 wherein the closure means are rounded.

7. The site guard as recited in claim 2 wherein the fabric connector(s) is at least about two inches long and at least about one inch wide.

8. The site guard as recited in claim 2 wherein the fabric connector(s) is of a length sufficient to wrap over the hollow member when the member is placed over the site and secured in place by the closure means.

9. The site guard as recited in claim 8 wherein the fabric connector(s) further comprises a window.

10. The site guard as recited in claim 8 further comprising retaining means.

11. The site guard as recited in claim 10 wherein the retaining means is selected from the group consisting of a channel, a guiding hook and a belt loop.

12. The site guard as recited in claim 2 wherein the closure means is selected from the group consisting of hook and loop fasteners, peel and stick tape, ties, pins, and clips.

13. The site guard as recited in claim 2 wherein the fabric connector(s) is splayed.

14. The site guard as recited in claim 1 further comprising a cushion on all or part of the edge of the hollow member.

15. The site guard as recited in claim 14 wherein the cushion is selected from the group consisting of cloth, gauze, stretch wrap, and foam tape.

16. The site guard as recited in claim 1 wherein the hollow member has an elongated closed end, the base is U-shaped, and the base is split into two legs so as to lay flush against a patient's skin when used.

17. The site guard as recited in claim 1 wherein the hollow member further comprises at least one ventilation hole.

18. The site guard as recited in claim 17 wherein the ventilation hole is covered by a porous material.

19. The site guard as recited in claim 18 wherein the porous material is selected from the group consisting of plastic grid and nylon mesh.

20. The site guard as recited in claim 17 comprising a plurality of ventilation holes.

21. A method for protecting a site, comprising placing the site guard of claim 2 over the site.

22. The method as recited in claim 21, wherein a tubing at or near the site is also covered by the hollow member.

23. A site guard kit, comprising:
   a) a hollow member having a base with an edge to be positioned upon a patient adjacent a site, the base having a width sufficient to straddle the site and a length and a height sufficient to cover the site, the base joined to a sidewall to form a cover;
   b) a fabric connector having a closure means, wherein the connector is capable of holding the site guard in place over the site without the need for separate adhesive tape; and
   c) an agent.

24. The kit as recited in claim 23, wherein the agent is selected from the group consisting an antimicrobial, an antifungal, an antiviral, aloe, vitamin E, and combinations of any of the foregoing.

25. A site guard kit, comprising:
   a) a hollow member having a base with an edge to be positioned upon a patient adjacent a site, the base having a width sufficient to straddle the site and a length and a height sufficient to cover the site, the base joined to a sidewall to form a cover;
   b) a fabric connector having a closure means, wherein the connector is capable of holding the site guard in place over the site without the need for separate adhesive tape; and
   c) a cushion on all or part of the edge of the hollow member.

26. The site guard as recited in claim 25, wherein the cushion is selected from the group consisting of cloth, gauze, stretch wrap, and foam tape.

27. A site guard kit, comprising:
   a) a hollow member having a base with an edge to be positioned upon a patient adjacent a site, the base having a width sufficient to straddle the site and a length and a height sufficient to cover the site, the base joined to a sidewall to form a cover;
   b) a fabric connector having a closure means, wherein the connector is capable of holding the site guard in place over the site without the need for separate adhesive tape;
wherein the hollow member has an elongated closed end, the base is U-shaped, and the base is split into two legs so as to lay flush against a patient's skin when used.

28. A site guard kit, comprising:
a) a hollow member having a base with an edge to be positioned upon a patient adjacent a site, the base having a width sufficient to straddle the site and a length and a height sufficient to cover the site, the base joined to a sidewall to form a cover;
b) a fabric connector having a closure means, wherein the connector is capable of holding the site guard in place over the site without the need for separate adhesive tape;
c) at least one ventilation hole, wherein the ventilation hole is covered by a porous material.

29. The site guard as recited in claim 28, wherein the porous material is selected from the group consisting of plastic grid and nylon mesh.

30. A site guard kit, comprising:
a) a hollow member having a base with an edge to be positioned upon a patient adjacent a site, the base having a width sufficient to straddle the site and a length and a height sufficient to cover the site, the base joined to a sidewall to form a cover;
b) a fabric connector having a closure means, wherein the connector is capable of holding the site guard in place over the site without the need for separate adhesive wherein the fabric connector further comprises a window.

31. A site guard kit, comprising:
a) a hollow member having a base with an edge to be positioned upon a patient adjacent a site, the base having a width sufficient to straddle the site and a length and a height sufficient to cover the site, the base joined to a sidewall to form a cover;
b) a fabric connector having a closure means, wherein the connector is capable of holding the site guard in place over the site without the need for separate adhesive tape;

wherein the fabric connector further comprises a pocket adapted to contain the hollow member.

* * * * *